US00PP18195P2

(12) United States Plant Patent
Kitajima

(10) Patent No.: US PP18,195 P2
(45) Date of Patent: Nov. 13, 2007

(54) ***CATHARANTHUS* PLANT NAMED 'SAKURAI 01'**

(50) Latin Name: *Catharanthus pacifica×roseus*
Varietal Denomination: SAKURAI 01

(76) Inventor: Osamu Kitajima, 201 Migatta, Sakurai, Nara (JP), 633-0085

( * ) Notice: Subject to any disclaimer, the term of this patent is extended or adjusted under 35 U.S.C. 154(b) by 44 days.

(21) Appl. No.: 11/442,435

(22) Filed: May 26, 2006

(51) Int. Cl.
*A01H 5/00* (2006.01)

(52) U.S. Cl. ..... Plt./263

(58) Field of Classification Search ..... Plt./263
See application file for complete search history.

*Primary Examiner*—Kent Bell
*Assistant Examiner*—Annette H Para

(57) ABSTRACT

A new cultivar of *Catharanthus* named 'SAKURAI 01' that is characterized by sterility, upright habit, dark-green foliage, pale green stems, and profuse red-purple flowers. In combination these traits set 'SAKURAI 01' apart from all other existing varieties of *Catharanthus* known to the inventor.

2 Drawing Sheets

Genus: *Catharanthus*. Species: *pacifica×roseus*.
Denomination: 'SAKURAI 01'.

BACKGROUND OF THE INVENTION

The present invention relates to a new and distinct cultivar of Madagascar periwinkle that is grown for use as a patio plant, container plant, or bedding plant for the landscape. The new cultivar is known botanically as *Catharanthus pacifica×roseus,* and will be referred to hereinafter by the cultivar name 'SAKURAI 01'.

'SAKURAI 01' is characterized, by sterility, upright habit, dark-green foliage, pale green stems, and profuse mid pink flowers. The cultural requirements are well-drained soil, shade, and full sun in cooler climates, as well as little to moderate water. 'SAKURAI 01' exhibits no pest or disease problems known to the inventor and is tender to cold temperatures but will tolerate heat.

The new *Catharanthus* cultivar 'SAKURAI 01' is a hybrid that resulted from the inter-specific cross-pollination of an unnamed and unreleased plant of the species *Catharanthus pacifica* and an individual unnamed and unreleased plant of the species *Catharanthus roseus.* The seeds that resulted from the cross-pollination were sown, producing a crop of seedlings. In 2000 the inventor selected from the seedlings, the single hybrid 'SAKURAI 01' described herein. The selection took place in a cultivated area of Sakurai, Nara, Japan. Selection was based on the distinguishing characteristics of flower color and sterility and tepal margin.

The female parent is a single unnamed plant of the species *Catharanthus pacifica* (unpatented) and the male parent plant is a single unnamed plant of the species *Catharanthus roseus* (unpatented). The closest comparison plant is the female parent *Catharanthus pacifica.* Whereas *Catharanthus pacificia* is fertile and has flat or planar flowers, 'SAKURAI 01' is sterile and bears wavy flowers whose petals appear creased and have sinuate tepal margins. This latter characteristic also distinguishes 'SAKURAI 01' from the male parent *Catharanthus roseus.*

The first asexual propagation of 'SAKURAI 01' was conducted by the inventor in 2000 in a cultivated area of Sakurai, Nara, Japan. The method of propagation used was vegetative cuttings. Since that time, under careful observation, the distinguishing characteristics have been determined stable, uniform and true to type in successive generations.

SUMMARY OF THE INVENTION

The following represent the distinguishing characteristics of the new *Catharanthus* cultivar 'SAKURAI 01'. In combination these traits set 'SAKURAI 01' apart from all other existing varieties of *Catharanthus* known to the inventor. 'SAKURAI 01' has not been tested under all possible conditions and phenotypic differences may be observed with variations in environmental, climatic, and cultural conditions, however, without any variance in genotype.

1. *Catharanthus* 'SAKURAI 01' is sterile.
2. *Catharanthus* 'SAKURAI 01' is evergreen.
3. *Catharanthus* 'SAKURAI 01' exhibits profuse mid pink flowers.
4. *Catharanthus* 'SAKURAI 01' flowers exhibit a combination of irregular lobules and weakly sinuate margin on each individual tepal.
5. *Catharanthus* 'SAKURAI 01' exhibits an upright habit.
6. *Catharanthus* 'SAKURAI 01' exhibits pale green stems and dark-green foliage.
7. *Catharanthus* 'SAKURAI 01' is 30 cm. in height and 40 cm. in width in an 18 cm. container.
8. The cultural requirements of *Catharanthus* 'SAKURAI 01' are well-drained soil, shade, to full sun in cooler climates, and little to moderate water.
9. *Catharanthus 'SAKURAI* 01' is an annual plant suitable for use as a patio plant, container plant or bedding plant for the landscape, or as a perennial in USDA hardiness zone 10 and warmer.

BRIEF DESCRIPTION OF THE DRAWINGS

The accompanying color drawings labeled as FIG. 1 and FIG. 2, illustrate the overall appearance of the new *Catha-*

*ranthus* cultivar 'SAKURAI 01', showing the colors as true as it is reasonably possible to obtain in colored reproductions of this type. Colors in the drawings may differ from the color values cited in the detailed botanical description, which accurately describe the actual colors of the new variety 'SAKURAI 01'. Plants in the drawings were grown under greenhouse conditions in Sakurai, Nara, Japan. Rooted vegetative cuttings were planted in 9 cm. containers in October 2005 and were transplanted to 18 cm. containers in January 2006. The plants were kept in a greenhouse and pinched back several times before the drawings were made, in April 2006.

The drawing labeled

The drawing labeled

Figure 1:
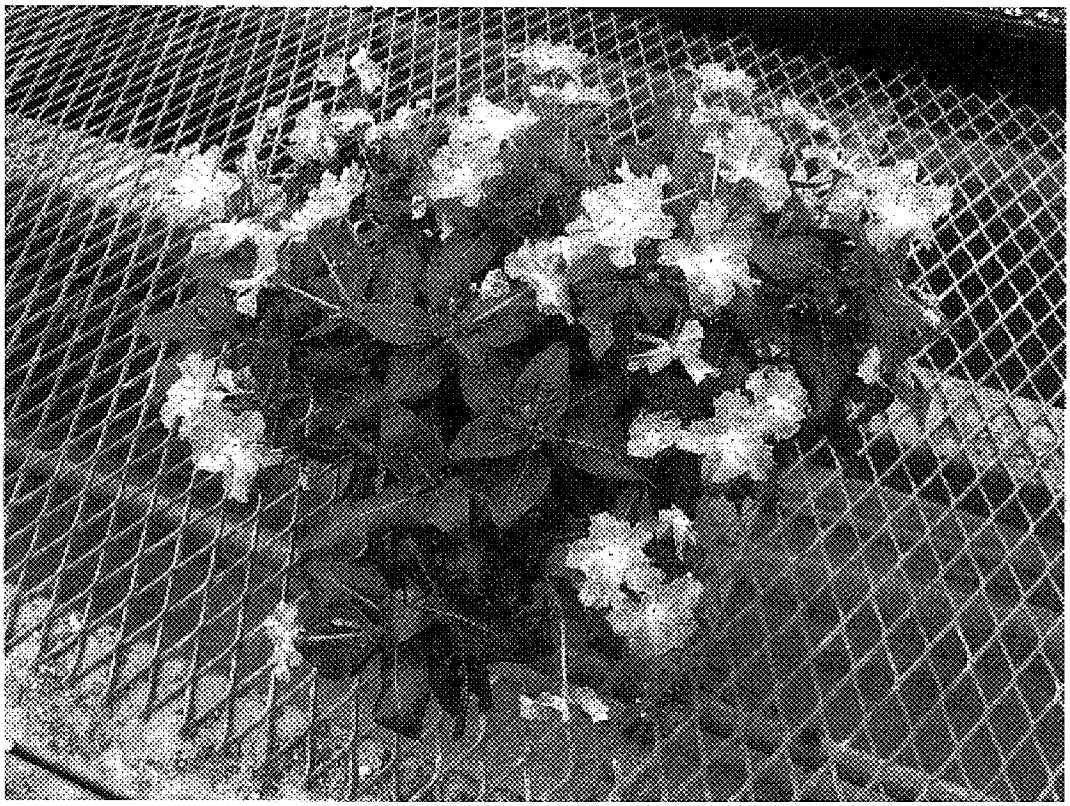
FIG. 1 illustrates the entire plant in bloom from a side perspective. The plant in the drawing is approximately 7-months-old.
Figure 2:
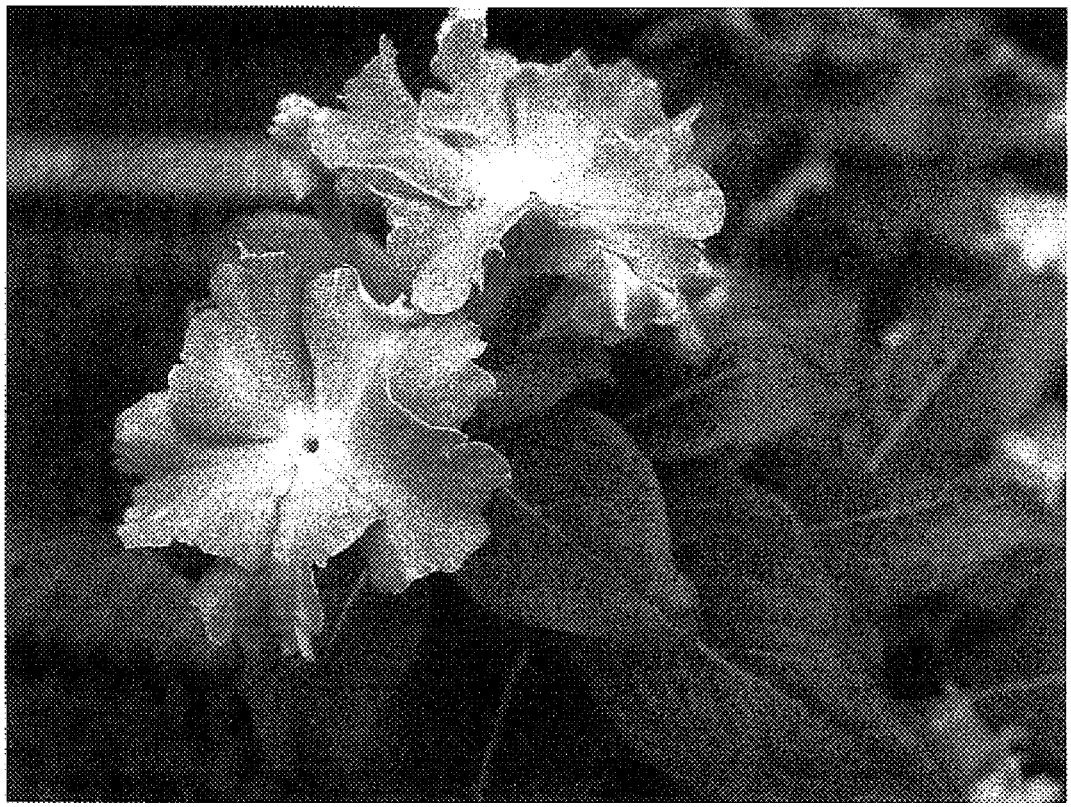
FIG. 2 illustrates a close-up view of the flowers of 'SAKURAI 01'.

Both drawings were made using conventional techniques and although foliage colors may appear different from actual colors due to light reflectance, they are as accurate as possible by conventional photography.

BOTANICAL DESCRIPTION OF THE PLANT

The following is a detailed description of the *Catharanthus* cultivar named 'SAKURAI 01'. Data was collected in Sakurai, Nara, Japan from 7 month old plants which had been grown as follows: Rooted vegetative cuttings were planted in 9 cm. containers in October 2005 and were transplanted to 18 cm. containers in January 2006. The plants were kept in a greenhouse and pinched back several times and observed during April 2006. Color determinations are in accordance with the 2001 edition of The Royal Horticultural Society Colour Chart, except where general color terms of ordinary dictionary significance are used. The growing requirements are similar to the species.

Botanical classification: *Catharanthus pacifica×roseus* 'SAKURAI 01'.
Species: *pacifica×roseus*.
Denomination: 'SAKURAI 01'.
Commercial classification: Annual or perennial in USDA hardiness zone 10 and warmer.
Common name: Madagascar periwinkle; also erroneously as Vinca.
Uses: Patio plant, container plant, or bedding plant for the landscape.
Container size: Suggested size is 18-centimeter container.
Cultural requirements: Shade, full sun in cooler climates, any well-drained soil, and little to moderate water.
Parentage: 'SAKURAI 01' is a hybrid that resulted from the cross-pollination of the following parent plants:
- *Seed parent.*—A plant of the species *Catharanthus pacifica*.
- *Pollen parent.*—A plant of the species *Catharanthus roseus*.

Plant description:
- *Blooming seasons.*—Summer and fall.
- *Vigor.*—Vigorous.
- *Plant habit.*—Upright habit.
- *Height* (*2-liter container*).—30 cm. in height.
- *Width* (*2-liter container*).—40 cm. in width.
- *Hardiness.*—USDA Zone 10.
- *Propagation.*—Propagation is accomplished using vegetative cuttings.
- *Root system.*—Fibrous.
- *Time to initiate rooting.*—3 weeks are needed to produce roots on the initial cuttings.
- *Temperature to initiate rooting.*—The ideal air temperature for rooting under greenhouse conditions is 20° Centigrade.
- *Crop time.*—7 months are needed to produce a commercial 18 cm. container plant from an initial cutting.
- *Seasonal interest.*—Vibrant red-purple flowers in summer and fall.

Stem:
- *Stem diameter.*—0.25 cm. in diameter.
- *Stem length.*—20 cm. in length.
- *Shape.*—Cylindrical.
- *Surface.*—Fluted.
- *Pubescence.*—None observed.
- *Stem color.*—N144C.
- *Internodes.*—1.50 cm. between nodes.

Foliage:
- *Type.*—Evergreen.
- *Leaf arrangement.*—Leaves are arranged in a combination of opposite and whorled on an individual stem.
- *Leaf division.*—Simple.
- *Leaf shape.*—Broadly elliptic.
- *Leaf base.*—Obtuse.
- *Leaf apex.*—Acute.
- *Leaf venation.*—Pinnate.
- *Vein color* (*abaxial surfaces*).—145A.
- *Vein color* (*adaxial surfaces*).—145A.
- *Leaf surfaces* (*adaxial*).—Puberulent.
- *Leaf surfaces* (*abaxial*).—Puberulent.
- *Leaf margins.*—Entire.
- *Leaf attachment.*—Petiolate.
- *Petiole dimensions.*—0.50 cm. in length and 2.75 mm. in width.
- *Petiole shape.*—Flattened oval.
- *Petiole color.*—145A.
- *Petiole surface.*—Puberulent.
- *Leaf color* (*adaxial surfaces*).—Colors 137A and 145A are individually present on adaxial surfaces.
- *Leaf color* (*abaxial surfaces*).—Colors 138A and 145A are individually present on abaxial surfaces.
- *Leaf appearance* (*abaxial surfaces*).—Satin.
- *Leaf appearance* (*adaxial surfaces*).—Semi-gloss.
- *Leaf length.*—Leaves range from 3.75 cm. to 5 cm in length.
- *Leaf width.*—Leaves range from 2 cm. to 2.50 cm. in width.
- *Average number of leaves per stem.*—An average of 32 leaves per stem.
- *Foliar fragrance.*—Pungent scent.

Flower:
- *Inflorescence.*—Solitary flower.
- *Petals.*—Apetalous.
- *Tepals.*—Five in number.
- *Fused or unfused.*—Tepals are unfused.
- *Tepal margin.*—Each individual tepal exhibits a combination of irregular lobules and weakly sinuate margin.
- *Tepal apex.*—Closest to obcordate.
- *Tepal base.*—Truncate.
- *Tepal surfaces* (*adaxial surfaces*).—Glabrous.
- *Tepal surfaces* (*abaxial surfaces*).—Glabrous.
- *Tepal shape.*—Closest to rhombic.

*Tepal dimensions.*—1.50 cm. in width and 1.50 cm. in length.

*Tepal color* (*adaxial surface*).—68B, fading to white towards tepal base with age and in full sun.

*Tepal color* (*abaxial surface*).—Very pale red-purple (paler than 69D) becoming darker, 69B, towards tepal apex.

*Aspect.*—Facing upward.

*Flower shape.*—Rotate.

*Flower color* (*adaxial surface*).—68B until aged, then 68B and white towards center.

*Flower color* (*abaxial surface*).—69D and 69B or paler.

*Color of peduncle.*—N144C.

*Peduncle length.*—Individual peduncles on an individual plant range from 2–3 cm. in length.

*Peduncle diameter.*—2 mm. in diameter.

*Peduncle shape.*—Cylindrical.

*Persistent or self-cleaning.*—Persistent.

*Dimensions of flower.*—1.75 cm. in depth and 3.50 cm. in diameter.

*Quantity of flowers* (*18 cm. container*).—Quantity ranges from 50–60 individual flowers on an individual commercial container plant.

*Bud color.*—145C.

*Bud apex.*—Truncate.

*Bud surface.*—Mostly glabrous with only a few hairs.

*Bud shape.*—Quadrate.

*Bud dimensions.*—0.75 cm. in length and 0.25 cm. in width.

*Sepals.*—None observed.

*Fragrance.*—None observed.

Reproductive organs:

*Stamens.*—None observed.

*Anthers.*—None observed.

*Stigma.*—None observed.

*Style.*—None observed.

*Ovary position.*—Inferior.

*Ovary shape.*—Closest to elongated oval in shape.

*Ovary dimensions.*—6 mm. in height and 3 mm. in width.

*Ovary color.*—N144C.

Seed: 'SAKURAI 01' is sterile and does not produce seed.

It is claimed:

1. A new and distinct variety of *Catharanthus* plant named 'SAKURAI 01' as described and illustrated.

* * * * *